United States Patent
Yost et al.

(12)

(10) Patent No.: US 6,542,242 B1
(45) Date of Patent: Apr. 1, 2003

(54) MAPPING AIR CONTAMINANTS USING PATH-INTEGRATED OPTICAL REMOTE SENSING WITH A NON-OVERLAPPING VARIABLE PATH LENGTH BEAM GEOMETRY

(75) Inventors: Michael G. Yost, Mercer Island, WA (US); Ram A. Hashmonay, Chapel Hill, NC (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 09/569,575

(22) Filed: May 10, 2000

Related U.S. Application Data

(60) Provisional application No. 60/133,317, filed on May 10, 1999.

(51) Int. Cl.[7] .................................................. G01B 9/02
(52) U.S. Cl. ........................ 356/450; 356/451; 356/438
(58) Field of Search ................................. 356/450, 451, 356/437, 438; 250/338.5, 339.8, 343, 344, 345

(56) References Cited

U.S. PATENT DOCUMENTS

| | | | | |
|---|---|---|---|---|
| 3,925,666 A | * | 12/1975 | Allan et al. | 250/338.5 |
| 4,426,640 A | * | 1/1984 | Becconsall et al. | 356/437 |
| 4,795,253 A | * | 1/1989 | Sandridge et al. | 356/451 |

* cited by examiner

*Primary Examiner*—Samuel A. Turner
(74) *Attorney, Agent, or Firm*—Ronald M. Anderson

(57) ABSTRACT

Path Integrated Optical Remote Sensing (PI-ORS) instruments are used to provide Path Integrated Concentration (PIC) data corresponding to a particulate concentration in region scanned by a sequence of optical beams. Prior art methods of developing spatial concentration maps using PIC data have required a relatively large number of intersecting beam paths. The present invention can produce spatial concentration maps using considerably fewer optical beams. Preferably, a non-overlapping radial beam geometry is used to produce PIC data that are processed to produce a spatial concentration map. The PIC data are indicative of the cumulative spatial concentration distribution of the contaminant in the sampling region. Once the PIC data are obtained, a specifically developed reconstruction algorithm is applied to the PIC data to create a map of concentration or contaminants or other constituents in the sampling region. Any of several different reconstruction algorithms can be employed. In general, a method for fitting or interpolating is used to estimate the cumulative distribution function of the contaminants or constituents of interest over the sampling region from the observed PIC data. Continuous or spline functions can be used in the reconstruction algorithm. Preferably, a smooth basis function minimization (SBFM) algorithm is used to fit a superposition of the integrated basis functions to the PIC data. The evaluation of the directional derivatives for the fitted integrated (cumulative) basis functions provides the desired map of concentration values over the sampling region. Using far fewer sources and detectors than the prior art, reasonably accurate concentration mappings can be achieved.

43 Claims, 12 Drawing Sheets

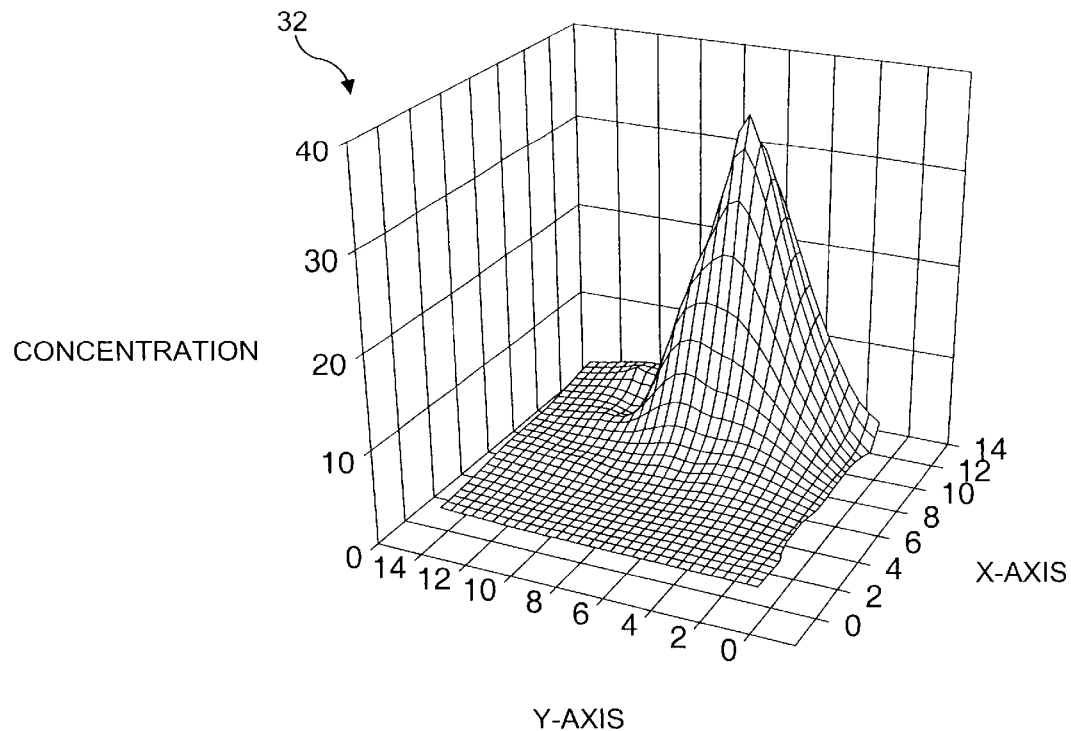
*FIG. 5A*    *REAL MAP*
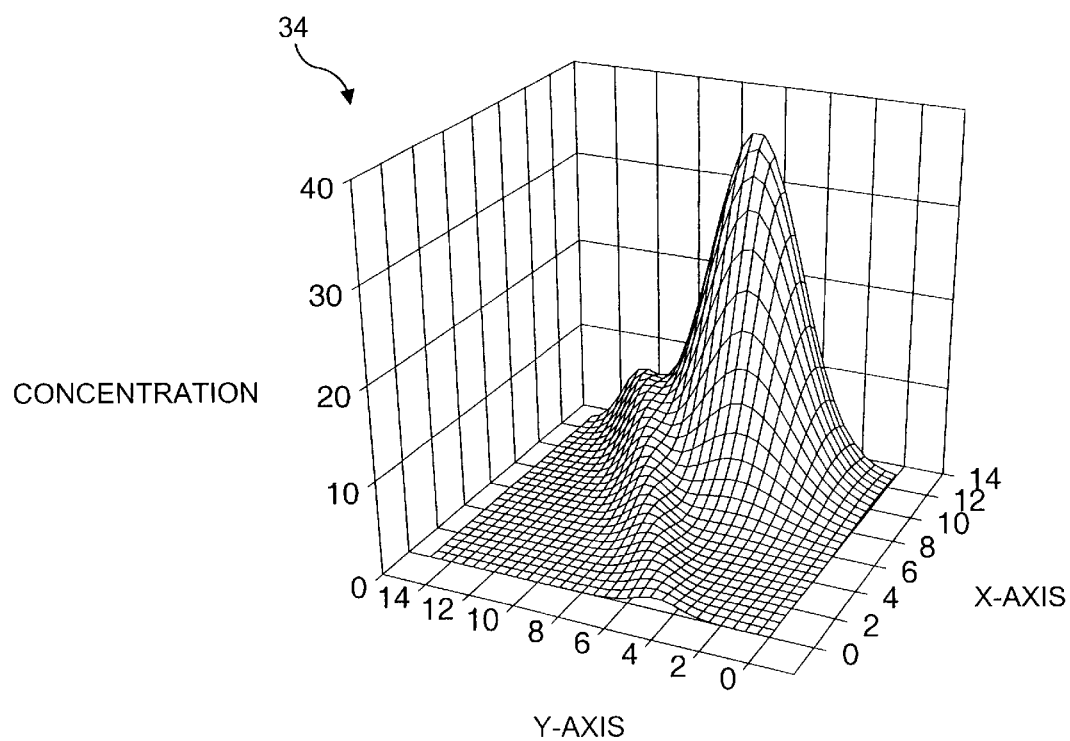
*FIG. 5B*    *SYNTHETIC MAP*

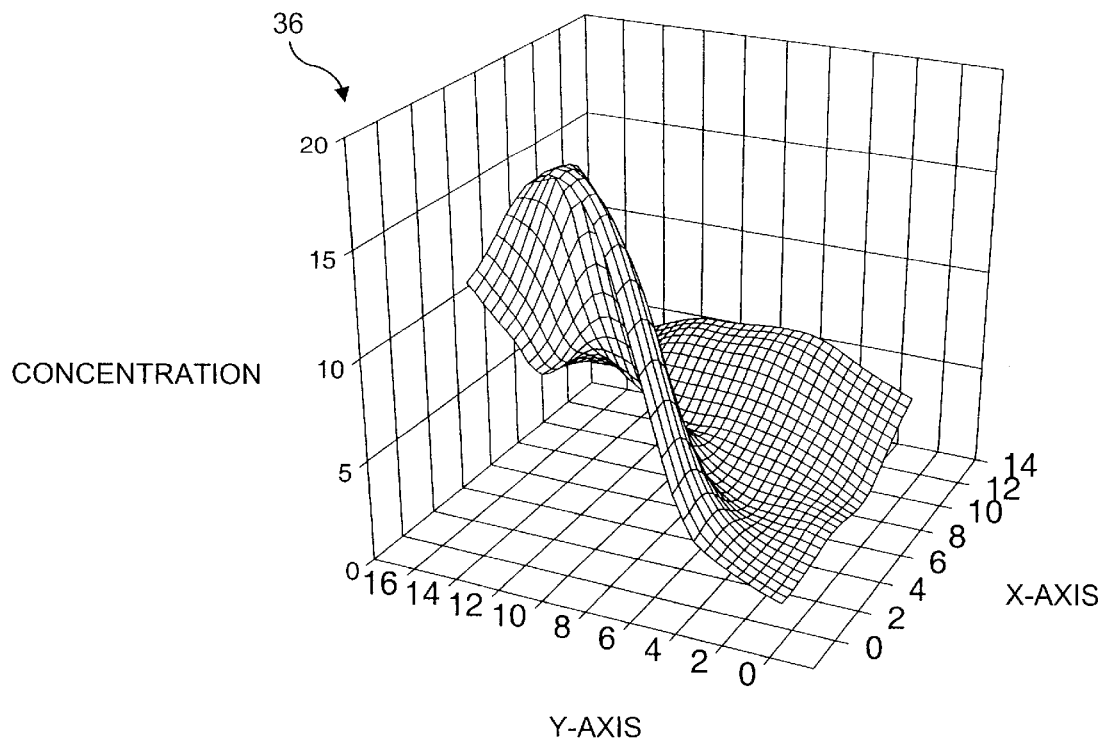
FIG. 6A    REAL MAP
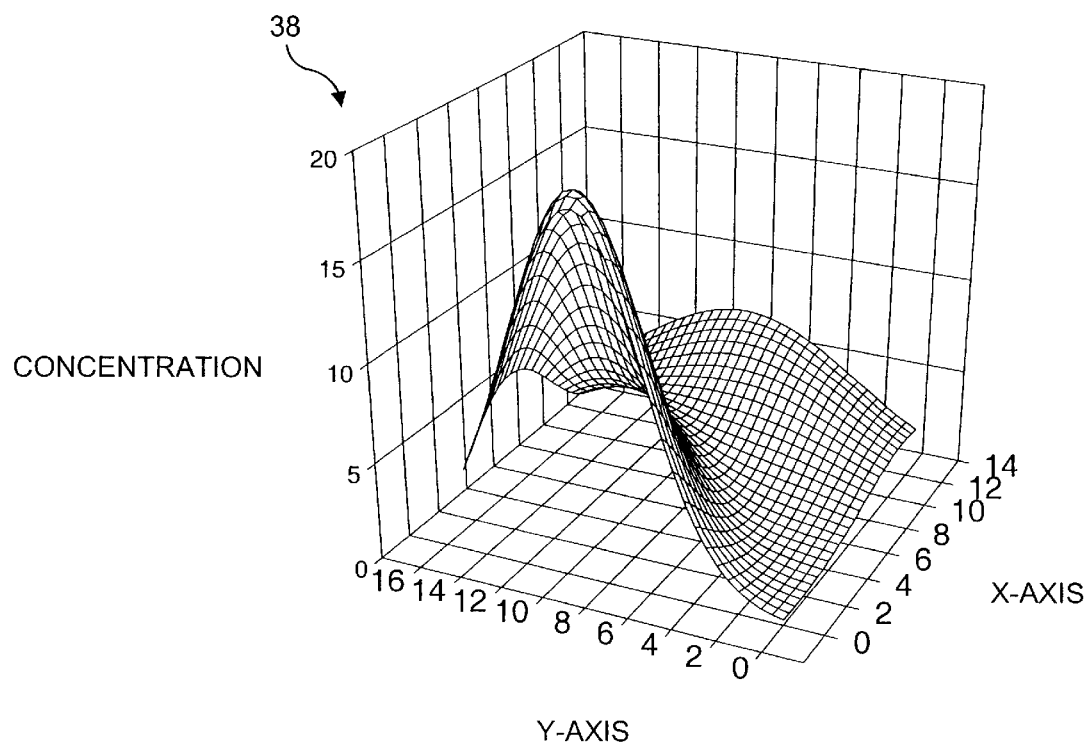
FIG. 6B    SYNTHETIC MAP

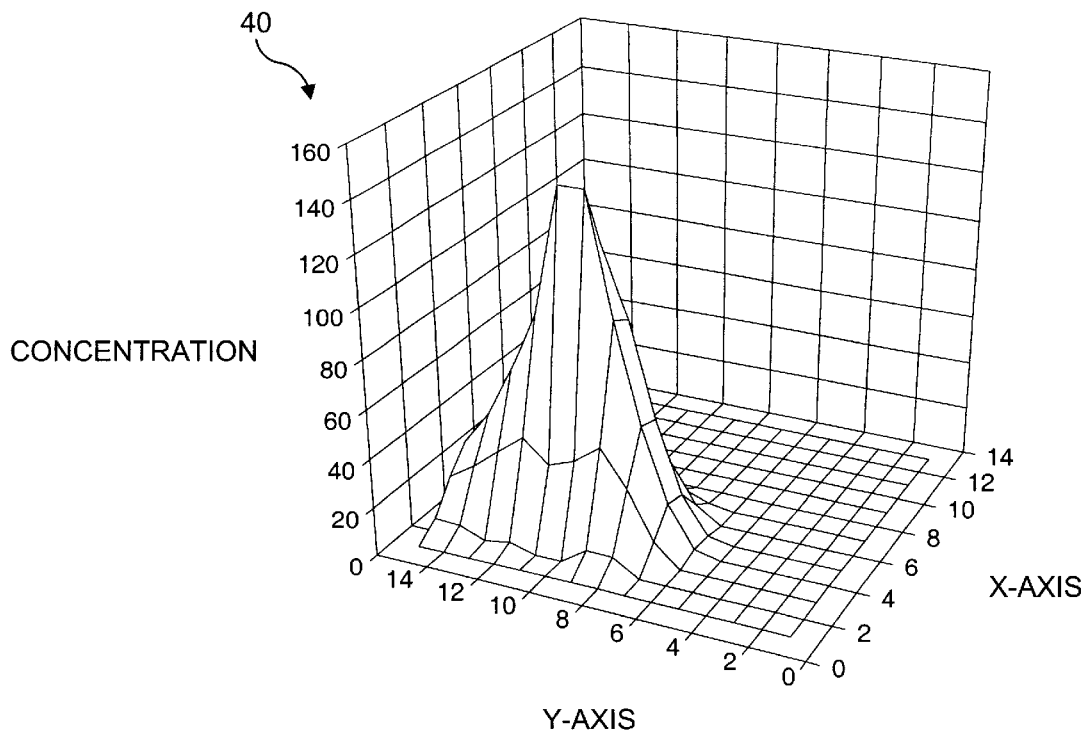
FIG. 7A    REAL MAP
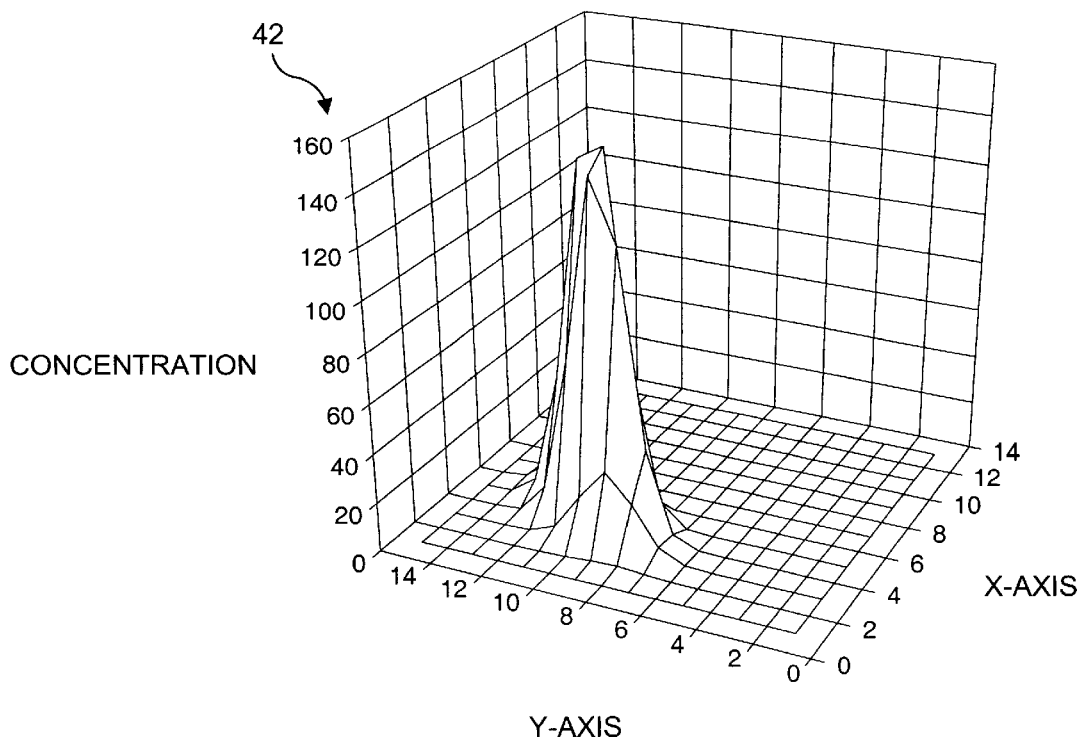
FIG. 7B    EXPERIMENTAL DATA MAP

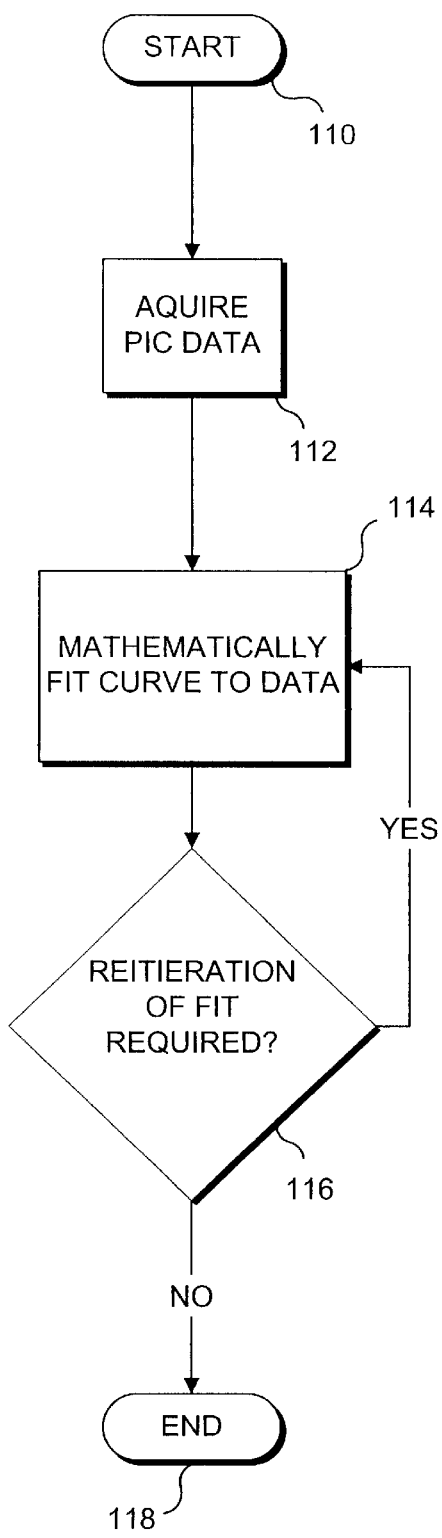
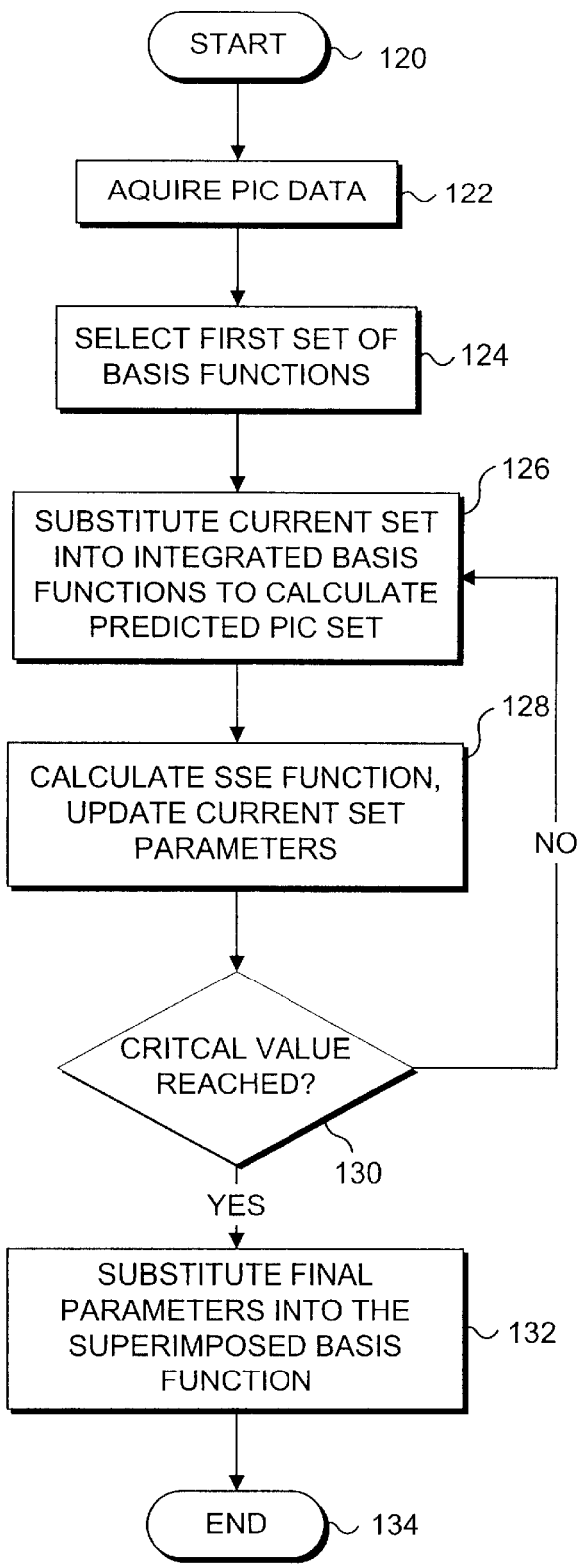
*FIG. 8*                *FIG. 9*

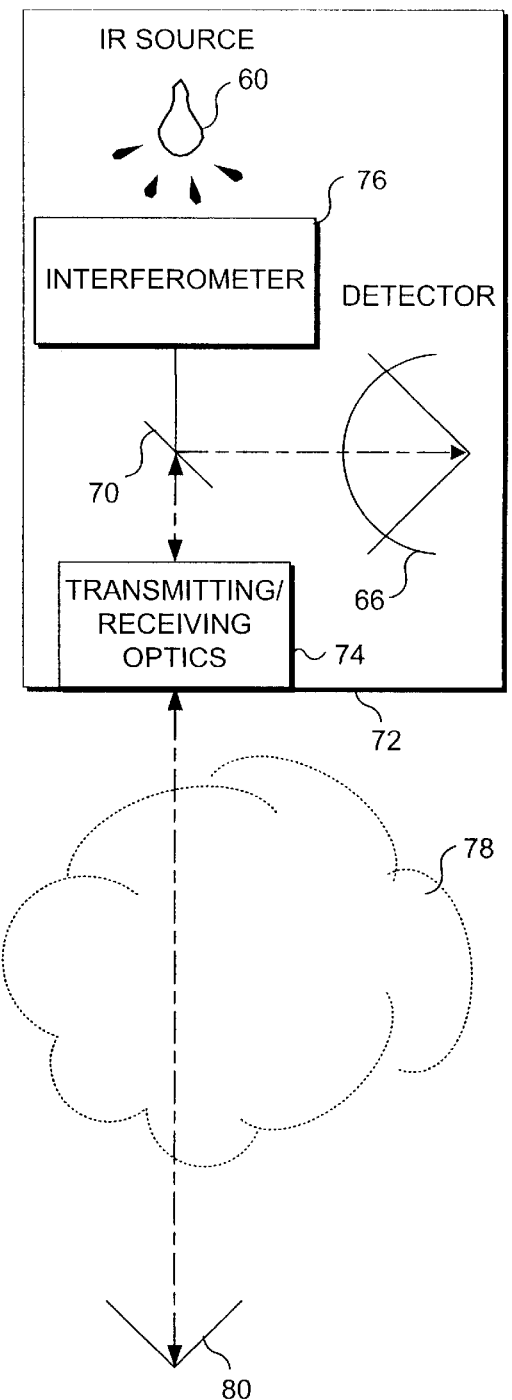
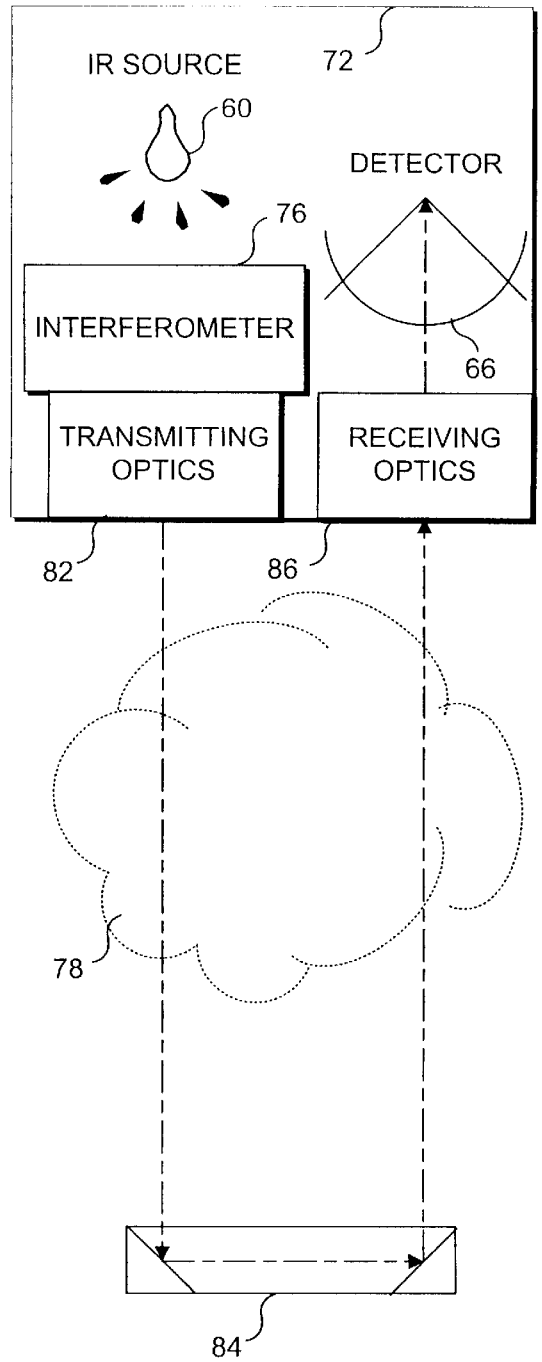
*FIG. 11A*  *FIG. 11B*

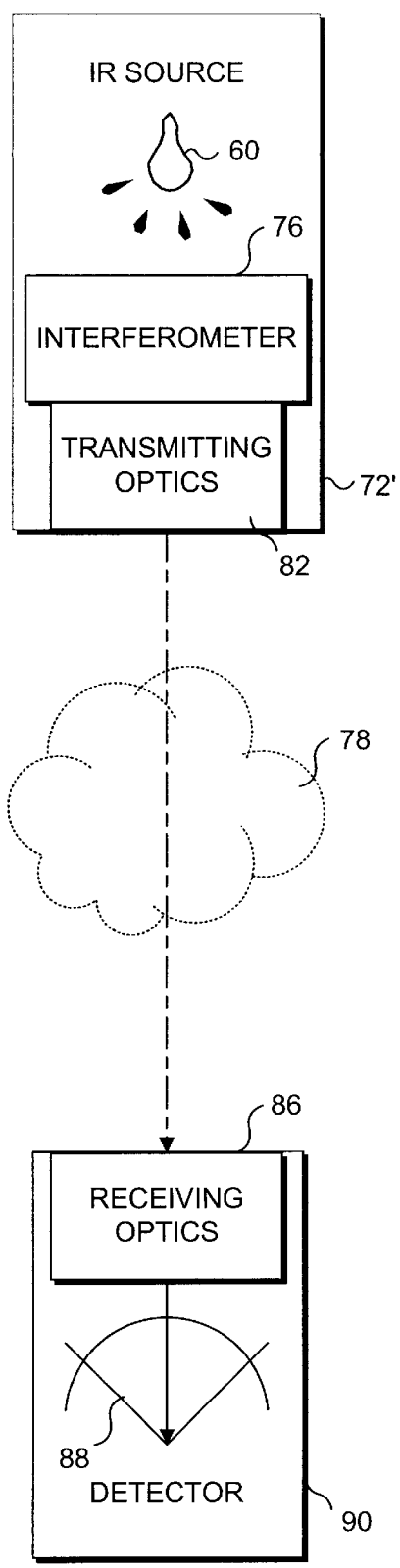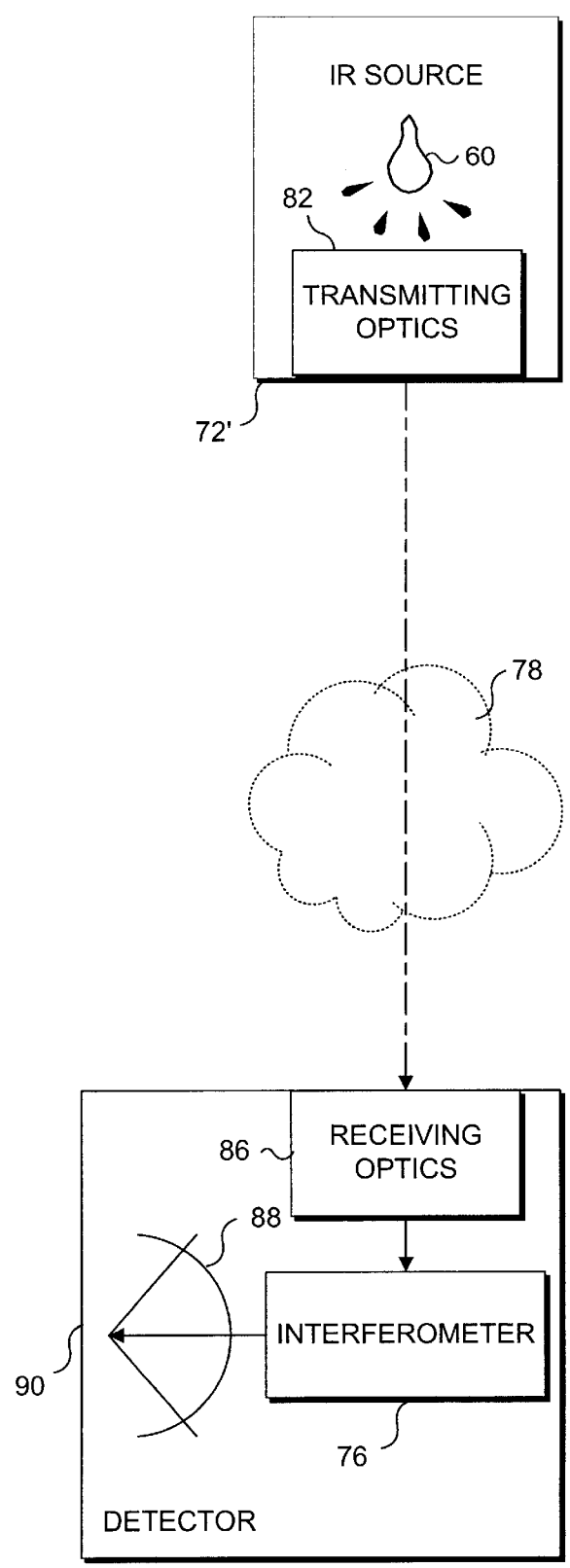
*FIG. 12A*  *FIG. 12B*

MAPPING AIR CONTAMINANTS USING PATH-INTEGRATED OPTICAL REMOTE SENSING WITH A NON-OVERLAPPING VARIABLE PATH LENGTH BEAM GEOMETRY

RELATED APPLICATIONS

This application is based on prior copending U.S. provisional patent application Ser. No. 60/133,317, filed May 10, 1999, the benefit of the filing date of which is hereby claimed under 35 U.S.C. §119(e).

FIELD OF THE INVENTION

The present invention generally relates to optical sensing systems for sensing gases or particulates entrained in a fluid, and more specifically, to a method for developing a detailed spatial data map of a specific gas concentration or particulate concentration within a fluid by using a relatively simple optical beam geometry.

BACKGROUND OF THE INVENTION

A variety of instruments developed for the optical remote sensing of atmospheric contaminants produce measurements that integrate the contaminant concentration over the length of the optical beam path. Such measurements are commonly referred to as Path Integrated Optical Remote Sensing (PI-ORS) measurements, and have characteristic units of concentration times length, e.g. ppm-meters.

The beam paths used in such measurements can range from a few meters to several kilometers in length. Often, the measurements are interpreted by dividing the path-integrated measurement of contaminant concentration by the path length to obtain the average concentration over the path. While providing useful information, the average concentration data are often difficult to interpret, as it is generally preferably to know the contaminant concentration at specific locations over the measurement path, rather than just the average concentration for the entire path length. The prior art teaches that by using complex beam geometries with a variety of existing PI-ORS instrumentation, and Computed Tomography (CT), the path integrated concentration (PIC) measurement data can be converted into two-dimensional (2D) spatial maps to facilitate air pollution mapping that indicate the location of specific sources of air contamination in the area region being surveyed.

In order to apply conventional CT mathematical techniques to this type of measurement, the optical beam paths must be arranged so that multiple beams from a variety of projection viewpoints intersect or overlap. This requirement necessitates the use of multiple instruments and multiple detectors, or the use of complicated schemes for scanning and folding the beam paths with mirrors to achieve a dense overlapping beam geometry. The concept of combining PI-ORS and CT for mapping outdoor air contaminant concentrations was introduced in theoretical studies during the late 1970s. These studies were based on systems that included complex beam geometries requiring multiple mirrors and detectors. The optical systems proposed were difficult to align and maintain and were very costly. Furthermore, for path lengths much greater than a few tens of meters, alignment difficulties could render such complex beam-based systems essentially unworkable.

In view of the problems with such prior art optical systems, it clearly would be desirable to develop a method for obtaining and manipulating PI-ORS data to produce spatial maps without the need for a complex beam arrangement to provide PIC data. Preferably, such a method should rely on a far simpler beam geometry, using radial beam paths of varying length, projected outward over the sampling area from a single source. Such a simple beam geometry, in combination with various conventional reconstruction algorithms, or an algorithm specifically designed for a radial non-overlapping beam geometry, should facilitate more rapid data collection, and should be usable both for indoor and outdoor applications. A simple radial beam geometry also could be applied to retrieve one-dimensional (1D) reconstructions of the concentration profile along a fence line, street, of other linear region of interest. The prior art does not teach or suggest such a method.

SUMMARY OF THE INVENTION

In accord with the present invention, a method is defined for mapping contaminants within a sampling region using path-integrated data. The method includes the steps of providing an instrument capable of generating path integrated concentration (PIC) data within the sampling region, and using the instrument to acquire PIC data for a plurality of different paths from within and extending to the boundaries of the sampling region. A cumulative distribution function that fits the acquired PIC data is reiteratively generated. Using the cumulative distribution function, a map of the contaminants within the sampling region is created.

Although a preferred form of the invention employs a plurality of light beams to scan the sampling region, the instrument can produce an illuminating signal that is either an optical signal or an acoustic signal. The step of using the instrument to acquire PIC data comprises the steps of using the instrument to generate a first path having a first length, and then using the instrument to generate additional paths having different lengths within the sampling region. It is expected that the instrument will be used to generate at least three paths of different lengths for a 1D reconstruction. In one embodiment, the instrument used to acquire PIC data generates a plurality of non-intersecting paths. In addition, the plurality of paths are preferably arrayed about a substantially common origin.

An embodiment of the instrument includes an illuminating unit and a detector, and a reflective unit adapted to reflect a light signal emitted from the illuminating unit to the detector. In one embodiment, a reflective unit is provided for each of the plurality of paths and the reflective units are adapted to direct a signal emitted from the illuminating unit back to the detector. In this case, an orientation of the instrument varied to achieve different directions for each of the plurality of different paths.

The cumulative distribution function which is fitted to the observed PIC data can be specified by a matrix of discrete pixel values, a matrix of spline coefficients, as a continuous function, or as a set of overlapping smooth basis functions. The step of reiteratively generating the cumulative distribution function preferably continues so long as a level of improvement in the fit of the cumulative distribution function to the acquired PIC data between successive iterations exceeds a signal noise level associated with the instrument, or some other objective stopping criteria.

If known parameters for the contaminant distribution are used with said cumulative distribution function, fewer paths can be required to acquire the PIC data. For example, the known parameters may include the locations of contaminant source(s) within the sampling region or a concentration range of the contaminants within the sampling region.

Another aspect of the present invention is directed at apparatus for acquiring PIC data from within a sampling region and generating a spatial concentration map based on the PIC data. The apparatus includes an instrument for emitting energy along a path, at least one detector, a memory for storing machine instructions, and a processor coupled to the detector and the memory, for executing the machine instructions to carry out functions that are generally consistent with the method described above.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 5A illustrates an actual (or simulated) contaminant concentration map;

FIG. 5B illustrates a concentration map generated using path integrated data obtained from the contaminant concentration map of FIG. 5A, based upon a synthesis with the beam geometry illustrated in FIG. 2 and in accord with the present invention;

FIG. 6A illustrates an actual (or simulated) contaminant concentration map;

FIG. 6B illustrates a concentration map generated using path integrated data obtained from the contaminant concentration map of FIG. 6A, based upon a synthesis with the beam geometry illustrated in FIG. 2 and in accord with the present invention;

FIG. 7A illustrates a contaminant concentration map generated by collecting an array of point samples in a controlled environment;

FIG. 7B illustrates a contaminant concentration map for the controlled environment of FIG. 7A, of the experiment of FIG. 7A determined by applying a smooth basis function minimization algorithm to PIC data obtained using the beam geometry of FIG. 2 in accord with the present invention;

FIG. 8 is a flow chart showing the sequence of logical steps used to acquire and manipulate PIC data in accord with the present invention;

FIG. 9 is a flow chart showing the sequence of logical steps used to acquire and manipulate PIC data using a smooth basis function minimization algorithm in accord with the present invention, FIG. 10 schematically illustrates the components in an OP-FTIR instrument used in a preferred embodiment of the present invention;

FIGS. 11A and 11B illustrate typical remote sensing optical instruments, each being used with a reflector and having a configuration in which the illuminating source and the detector are combined in a single unit; and FIGS. 12A and 12B illustrate typical remote sensing optical instruments, each having a configuration in which the illuminating source and the detector are two distinct and separate units.

DESCRIPTION OF THE PREFERRED EMBODIMENT

Figure 1:
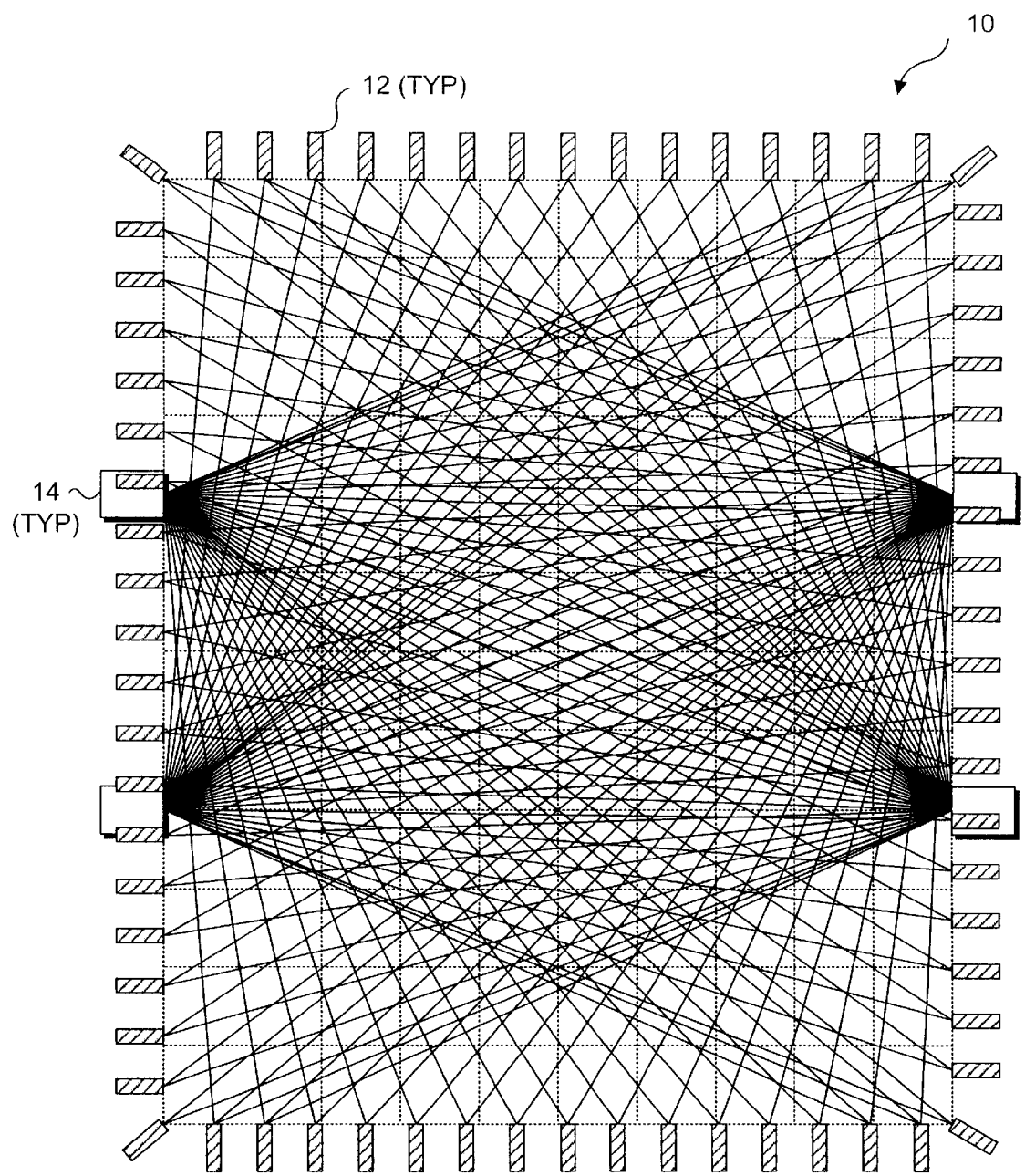
FIG. 1 (Prior Art) schematically illustrates a complex beam geometry employed in conventional systems for mapping air contaminant concentrations.

PI-ORS instruments can be used to provide PIC data indicative of a gas or particulate concentration in the air scanned by an optical beam. As noted above in the Background of the Invention, prior art methods of developing spatial concentration maps using PIC data employed a large number of sources or reflectors for producing many intersecting beam paths. In contrast, the present invention can produce spatial contaminant concentration maps using considerably fewer components and fewer optical beams. Preferably, in the present invention, a non-overlapping radial beam geometry is used in conjunction with a suitable mathematical algorithm to produce a spatial contaminant concentration map. The radial beam geometry of the present invention can be used with a variety of existing PI-ORS instruments, and is simpler and more practical than the complex beam geometries used in the past for CT air pollution mapping. Because only a single instrument is required, it is expected that PI-ORS systems based on the present invention will enable rapid mapping of air pollution data to be achieved, and will be useful in many other applications relating to the remote sensing of particulate concentration data, including particulates other than air contaminants. In connection with the broader application of the present invention, it will be understood that the terms "contamination" or "air contamination" are intended to encompass any type of gas or particulate concentration measurement in any type of fluid, not limited to air.

While a preferred embodiment of the present invention is applied to measuring air contaminants using electromagnetic sensing instruments, it is intended that the technique employed in the present invention can be applied to any measurement that produces results in the form of path integrated data. Other applications of the present invention will therefore extend to almost any other medium and to non-electromagnetic sensing methods. For example, acoustic or electromagnetic signals traveling in water could be used to reconstruct profiles of different properties of the medium (e.g. temperature, salinity, etc.) Similarly, this method can be used to process acoustic or seismic signals traveling in the earth, acoustic signals traveling in biological tissue, or in virtually any other solid medium.

A key element of the present invention is the ability to resolve extinction and adsorption values along individual beam paths. While prior art optical beam geometry systems often required the use of one hundred or more individual beam paths and several instruments, the present invention can operate successfully with comparatively fewer paths and a single instrument. As few as three beam paths can be applied to produce a 1-D reconstruction, and as few as six beam paths can be applied to produce a 2-D reconstruction, when employing the present invention with a smooth basis function minimization reconstruction method. Employing a larger number of paths will enhance the spatial resolution in the present invention. The spatial resolution is approximately equal to the root-mean-square (RMS) spacing of the detectors in FIG. 2. The present invention uses a PI-ORS instrument to scan and acquire PIC data from individual targets along different path lengths penetrating into the sampling region. Preferably, the instrument sequentially scans by directing light along each beam path in the sampling region and returns the observed PIC data for that path. A plurality of fixed, non-scanning instruments could be substituted for a single scanning instrument, or an instrument could be used that samples multiple beam paths in the field of view using an array detector system. The PIC data directly corresponds to the cumulative spatial concentration distribution of contaminants in the sampling region. Along the direction of each beam path from the origin at a moment in time, mass conservation requires that this cumulative distribution be a monotonic increasing function.

Preferably the instrument scans the sampling region as rapidly as possible to avoid temporal fluctuations in the concentration field during sampling time interval. These temporal fluctuations can add random errors and other inconsistencies to the PIC data, leading to artifacts or errors in the concentration map reconstructions, particularly if the region being scanned is in flux, such as would occur if a plume of contaminants from a smokestack is dispersed by the wind. A system that simultaneously measures a plurality of beam paths as described above will help minimize the time required for data collection.

Once the PIC data are obtained, a reconstruction algorithm is applied to the PIC data to create a map of the concentration field in the sampling region of one or two dimensions. The PI-ORS instrument can be situated in the middle, side, or corner of the sampling region. Several embodiments of reconstruction algorithms are possible. In general, some method of fitting or interpolation is used to estimate the cumulative distribution function of the air contamination over the sampling region from the observed PIC data. In the case of a cumulative function specified by discrete values, a conventional CT algorithm such as the maximum likelihood or multiplicative algebraic reconstruction technique (MART) can be used to fit the cumulative function. Continuous or spline functions can be used in the reconstruction algorithm as well.

In a preferred embodiment, a smooth basis function minimization (SBFM) algorithm is used to reconstruct the data concentration maps. The SBFM procedure fits a superposition of the integrated basis functions to the PIC data. The evaluation of the directional derivatives for the fitted integrated (cumulative) basis functions provides the desired map of concentration values over the sampling region, and the evaluation of the directional derivatives (concentration values) in the plane or along a line of measurement is done by substituting the fitted parameters in the superimposed basis functions.

While a preferred embodiment employs a SBFM, it should be understood that many different kinds of interpolation schemes (e.g. linear, quadratic, spline, etc.) provide satisfactory estimates of the cumulative spatial distribution necessary for predicting the field of concentrations over the sampling region. By analytically or numerically evaluating the directional derivatives from the origin to the location of a point estimate, a concentration field is obtained. However, it is not intended that the present invention be in any way limited to the specific design of the interpolation scheme discussed below.

DETAILS OF A PREFERRED EMBODIMENT

FIG. 1 illustrates a prior art beam configuration 10 that requires a substantial number of intersecting beam paths to generate sufficient PIC data to provide a spatial concentration map. As illustrated, the plurality of beam paths are generated by four PI-ORS instruments 14, and a large number of detectors 12. Those of ordinary skill in the art will appreciate that detectors 12 can by replaced by mirrors or retroreflectors that direct each optical beam back to a detector. Some PI-ORS instruments are designed to be used with mirrors or retroreflectors, and include sensing units within the instrument itself.

Figure 2:
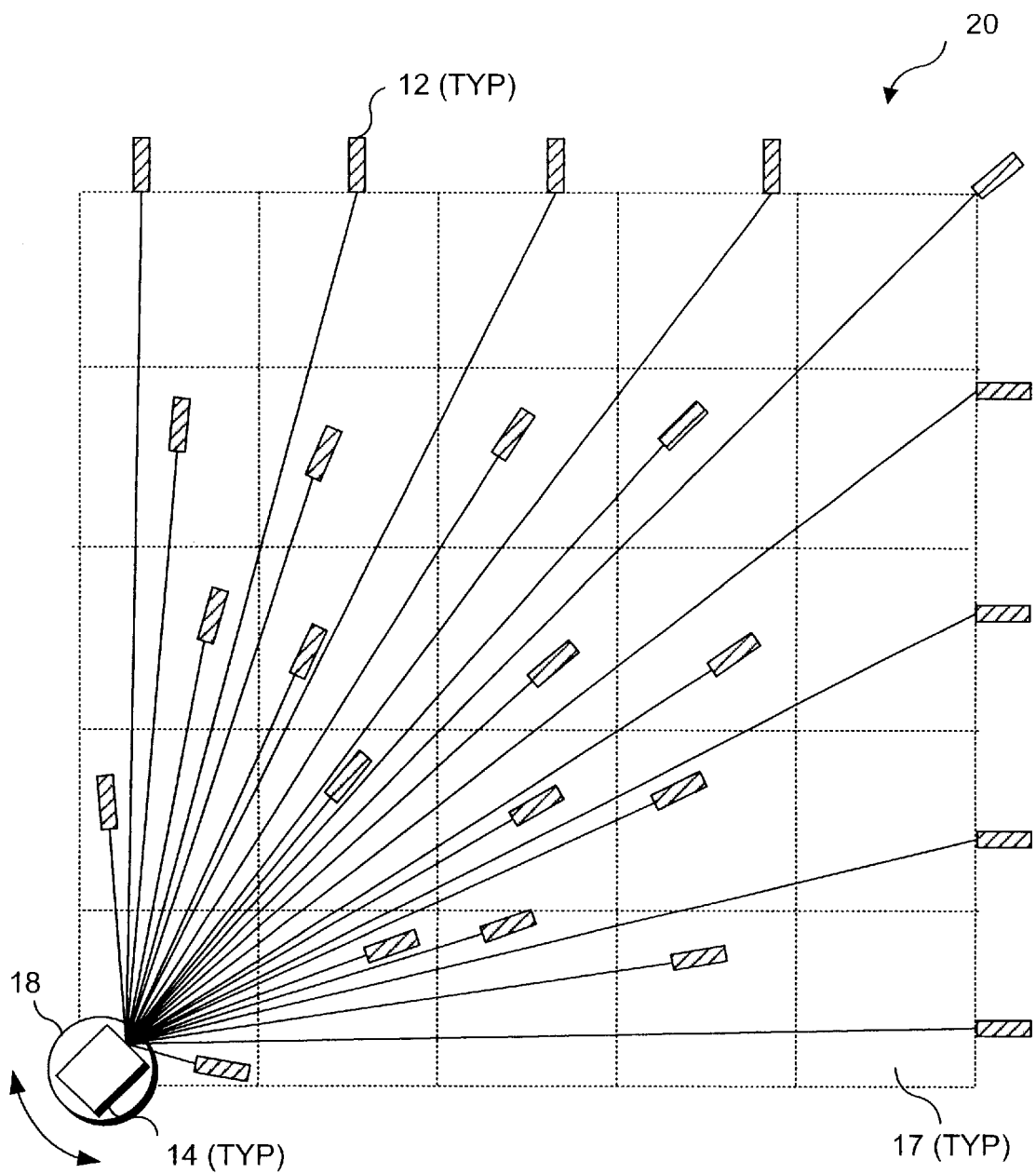
FIG. 2 schematically illustrates a 2D non-overlapping beam geometry in accord with the present invention, which can produce a map of air contaminant concentrations using only a single source and far fewer beam paths than the prior art system of FIG. 1.

FIG. 2 illustrates a radial beam configuration 20 in accord with the present invention that requires only a few non-intersecting beam paths to produce sufficient PIC data to generate a spatial contaminant or particulate concentration map. As illustrated, the plurality of beam paths are generated by a single PI-ORS instrument 14, and substantially fewer detectors 12 than were required in association with prior art beam configuration 10. Preferably the positions of detectors 12 are arranged so as to disperse the sampling beams as uniformly as possible over the sampling region, and minimize the RMS spacing of the detectors.

Note that PI-ORS instrument 14 is mounted on a turntable 18, that enables the single instrument to be easily repositioned to scan the plurality beam paths. If the desired configuration of the plurality of beam paths does not describe a plane, turntable 18 can be replaced with a gimbal mechanism, to enable the instrument to be easily positioned scan a plurality of beam paths in three dimensions. Furthermore, rather that mechanically repositioning the instrument itself, those of ordinary skill in the art will recognize that an instrument with a beam steering mechanism can be beneficially employed, so that a plurality of different beam paths can be scanned without physically moving the instrument.

Detectors 12 are generally photon detectors, although in some applications (in which the illuminating source instrument is capable of transmitting measurable thermal energy throughout the length of the beam path), thermal detectors are preferably used. Detectors 12 must be matched to the instrument that generates the beam path (the illuminating source instrument). For a preferred embodiment that is directed to generating a spatial map of a concentration plume within an air volume, instruments and detectors designed to operate in the mid-infrared range (wavelengths of 1.5–20 microns) are expected to be particularly useful. For studies involving determining ozone concentration, the ultraviolet range is expected to be useful.

It should be noted that a preferred embodiment is designed to determine a spatial concentration of contaminants or particulates in an air volume, for example, in studying or tracking air pollution. However, it should be understood that the present invention can also be applied for spatially mapping concentrations of constituents within solids and liquids as well. Those of ordinary skill in the art will readily understand that particular care must be taken to select an illuminating source capable of illuminating constituents within the target medium. Upon selecting an illuminating source and detectors matched to the target medium, a simple beam geometry such as that illustrated in FIG. 2 can be used with an algorithm discussed below to produce the desired concentration map. For example, using a blue-green laser as an illuminating source, the present invention could be used to generate a spatial concentration map of phytoplankton in seawater. It is further anticipated that the method of the present invention, which employs a simple beam geometry to develop spatial constituent concentration maps, could be employed in conjunction with illuminating sources and detectors that utilize x-rays or ultrasound.

It has been noted that the present invention requires significantly fewer beam paths than required by prior art methods. While FIG. 2 illustrates beam paths, as few as six beam paths can be used to generate useful spatial concentration maps of many types of air pollution plumes. Furthermore, if parameters about a particular plume are know, such as maximum concentration ranges, or information relating to the location of the plume, those parameters can be used in the data manipulation algorithm to develop the desired spatial concentration map, thereby reducing the minimum number of beam paths required. It should be noted that increasing the number of beam paths will generally increase the accuracy of any concentration spatial map generated. It should also be noted that using the simple optical beam path method of the present invention will enable the generation of concentration spatial maps of a quality comparable to that of maps generated using prior art beam configurations (with many beams and detectors), using considerably fewer beams than the prior art.

FIG. 2 illustrates a preferred embodiment of the present invention that uses non-intersecting beam paths. It should be noted the present invention does not require the use of non-intersecting beams, while in contrast, prior art beam configuration 10 (FIG. 1) does require the use of intersecting beams. The preferred radial beam configuration illustrated in FIG. 2 does not include intersecting beams because use of intersecting beams would increase the complexity of the beam pattern (requiring either an additional illuminating source or mirrors to cause beam paths to intersect), and not because intersecting beam paths are incompatible with the present invention. Thus, it should be understood that the present invention is not limited to non-intersecting beam configurations, but that the use of non-intersecting beam paths in the present invention enables very simple beam patterns to be employed to produce useful spatial concentration maps of contaminants or other constituents in a fluid.

Note that the sampling region illustrated in FIG. 2 is partitioned into twenty-five quadrants 17. A preferred beam geometry will include at least one beam path that terminates in each quadrant. In determining a beam geometry, one must first determine the resolution desired, as increasing the number of beam paths will increase the resolution. Having determined a desired resolution, one then selects the number of beam paths (or quadrants) to employ (fewer for less resolution, more for greater resolution). Of course, factors relating to the ability to place either a detector or reflector at a given location within the sampling region will also effect the beam geometry developed, as some quadrants may not be readily accessible. As noted above, as few as six beams can provide a useful 2D spatial concentration map.

In determining the beam geometry illustrated in FIG. 2, it was first decided that a greater resolution than is obtainable by using a minimal number of beams was desired. It was then determined that given the nature of the sampling region, that twenty-five beams could be readily employed. The sampling region was then divided into twenty-five quadrants, and a beam geometry was developed so that at least one beam terminated in each of the quadrants. Such a beam geometry is more likely to develop an accurate spatial map.

Dividing the sampling region into a number of similar size quadrants, such that more quadrants are included as more resolution is desired, and then terminating a beam in each quadrant, is not the only beam geometry that can be employed. Such an approach merely represents a preferred embodiment, because it ensures that data is obtained over the entire sampling region. However, it should be understood that useful spatial maps can still be produced if fewer beams are used, or if not all quadrants include a beam path that terminates in that quadrant. Note also that the number of beams does not have to equal the number of quadrants to develop a useful spatial map. Two or more beams terminating in each quadrant will result in an increase in spatial resolution, while less than one beam terminating in each quadrant will result in a decrease in spatial resolution; yet in each case (as long as the minimum number of beams is employed) a useful spatial map can be generated. Regardless of the number of beam paths employed, at least one path will extend to at least the boundary of the sampling region (at which point it can be reflected back into the sampling region) while at least one beam bath will not extend to the boundary of the sampling region, but rather terminate at a point within the interior of the sampling region.

In accord with the present invention, a series of 1D beam geometries can be employed to create a planar configuration with different path lengths extending along lines of sight within a plane, or a single line of sight, to provide a linear mapping. The linear mapping of concentration would be useful along a property line, for example, to map the concentration of contaminants along the property line of a manufacturing facility. The present invention is not limited to having a prescribed or "fixed" beam geometry. Even a geometry that has randomly arranged paths of varying length produces a reconstruction, and the path lengths can change from each round of scanning provided the orientation and length are known. While 1D and 2D reconstructions are discussed, it should be understood that a straightforward extension of the technique to both vertical and horizontal scanning arrangements can provide three-dimensional (3D) mapping capability. For example, simply shifting the geometry shown in FIG. 2 to different elevations relative to the surface of drawing sheet will provide 3D information. Alternatively, the beam can be caused to sequentially scan radially in three dimensions, rather than in a plane, e.g., from a corner of a cube comprising the sampling region.

In a preferred embodiment, the illuminating source (PI-ORS instrument 14) is an OP-FTIR. However, other optical (and non-optical, as discussed above) illuminating sources can also be used. The present invention can be practiced in conjunction with any optical remote-sensing device that produces PIC data with different path lengths. Sources suitable for practicing the present invention include Differential Optical Absorption Spectroscopy (DOAS) devices, Tunable Diode Lasers (TDL), backscatter Lidar, and Differential Absorption Lidars (DIAL) (using either aerosols or back-scattered signals from hard targets to map air-pollutants in a large scale).

OP-FTIR data are collected outdoors or indoors for environmental monitoring, and the OP-FTIR data are especially useful when mapping the concentration of more than one pollutant. Applying this mapping technology to a vertical plane downwind from an air pollution emission source in conjunction with wind data provides the emission flux from a point, line, or area source. As noted above, the spatial concentration mapping method of the present invention can be applied in one dimension to give a concentration profile along a single line of sight, for monitoring contaminant concentration along the fence line of an industrial plant or other area.

Preferably, one embodiment of a system used to implement the present invention includes multiple detectors or an array detector, while another embodiment employs multiple beam path sensing capability to enable simultaneous PIC data acquisition over some or all of the plural beam paths. The latter embodiment reduces or eliminates the need for sequentially scanning each beam path over the sampling region, results in faster data acquisition, and reduces potential inconsistencies in the PIC data due to temporal fluctuations in the concentration field during sampling.

Figure 3A:
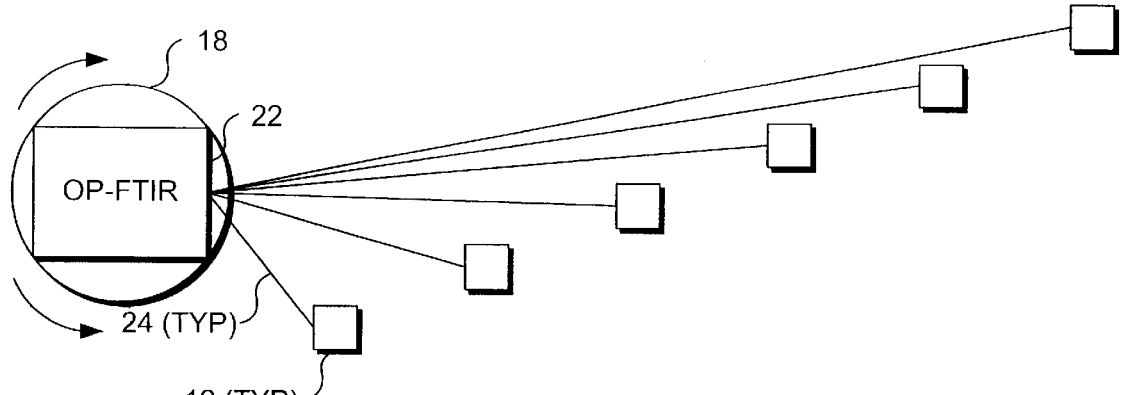
FIGS. 3A and 3B schematically respectively illustrate embodiments for a vertical plane geometry and a one-dimensional (1D) beam geometry, both using a scanning Open Path Fourier Transformation Infrared (OP-FTIR) instrument.

FIG. 3A illustrates an OP-FTIR instrument 22 being used to collect PIC data from a plurality of different beam paths 24. As discussed above, six beam paths of differing lengths are typically required to generate a useful 2D concentration map, although if additional parameters are known (plume location, or minimum/maximum concentration values in the plume), fewer beam paths can be used. It should be noted that the plurality of beam paths can be generated in a number of ways. As shown in FIG. 3A, only one OP-FTIR instrument 22 is employed. If a single OP-FTIR instrument is used, preferably the OP-FTIR instrument or the beam generated by it can be directed to different angles in a plane (or in three dimensions) so that sequential beam paths are directed in different directions through the sampling region, towards detectors (or reflectors) 12. Preferably, turntable 18 is used to rotate the OP-FTIR instrument in a plane, while a gimbaled mechanism (not shown) can be used to rotate the instrument to different angles in three dimensions. As noted above, turntable 18 or the related gimbaled mechanism can be replaced by selecting an OP-FTIR instrument whose beam can be optically steered.

Figure 3B:
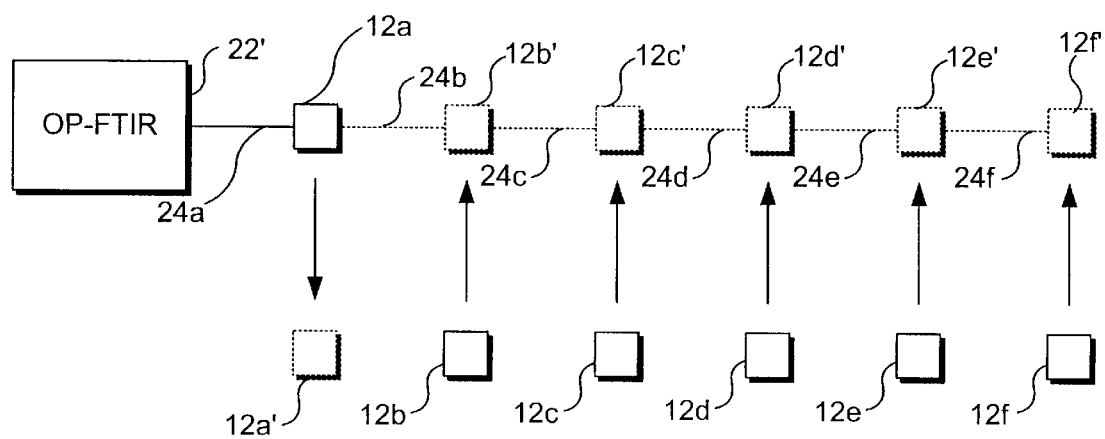

In FIG. 3B, a single fixed OP-FTIR instrument 22' is used with a plurality of detectors (or reflectors) 12a, 12b, 12c, 12d, 12e, and 12f, which are selectively moved in and out of the fixed direction optical beam, one at a time, to generate different beam path lengths 24a, 24b, 24c, 24d, 24e, and 24f, as is illustrated. The alternative position of each detector (or reflector) is indicated using a prime notation on the reference number, e.g., detector (or reflector) 12a'. Note that in FIGS. 3A and 3B, whether these detectors (or reflectors) are light sensitive transducers, mirrors, or retroreflectors depends purely on the design of the illuminating instrument (OP-FTIR instrument 22 or 22' in these two embodiments). Some instruments incorporate detectors, and are designed to be used with mirrors or retroreflectors. Other instruments do not incorporate detectors, and must be used in conjunction with separate detectors. It should also be noted that scanning multiple beam paths using only a single detector is possible if the position of the detector can be changed easily and quickly. It is anticipated that systems employing a plurality of detectors will be more convenient to operate, and will provide better data.

Once the PIC data, which represent the cumulative spatial distribution of a contaminant or other constituent over the sampling region, has been collected, the data are processed to provide a spatial concentration map. As noted above, one of several different types of interpolation procedures can be used to determine directional derivatives of the integrated path data to develop a concentration map. In a preferred embodiment, a smooth basis function minimization approach (SBFM) is used for this purpose. In the SBFM approach, a known continuous smooth basis function with unknown parameters is assumed to describe the spatial distribution of concentrations. The SBFM approach fits smooth functions with a limited number of overall parameters that satisfy the PIC data. Preferably, a superposition of bivariate Gaussian spatial distributions is selected as the basis function for a two dimensional reconstruction. Note that the smooth basis function could be one of many types of bivariate spatial distributions, or a superposition of several distributions having different parameters.

Depending upon the type of interpolation procedure that is selected, the process is iterated until a desired fit is achieved. The iteration process is terminated once results within the signal noise limits of the system have been achieved. For instance, for a given system, it might be expected that signal noise from the system will produce a 1% error. Under such circumstances, repeating the interpolation procedure once the level of improvement between successive iterations is reduced to 1% or less provides no benefit, since the result can not be any more accurate than the signal used to produce it.

Figure 4:
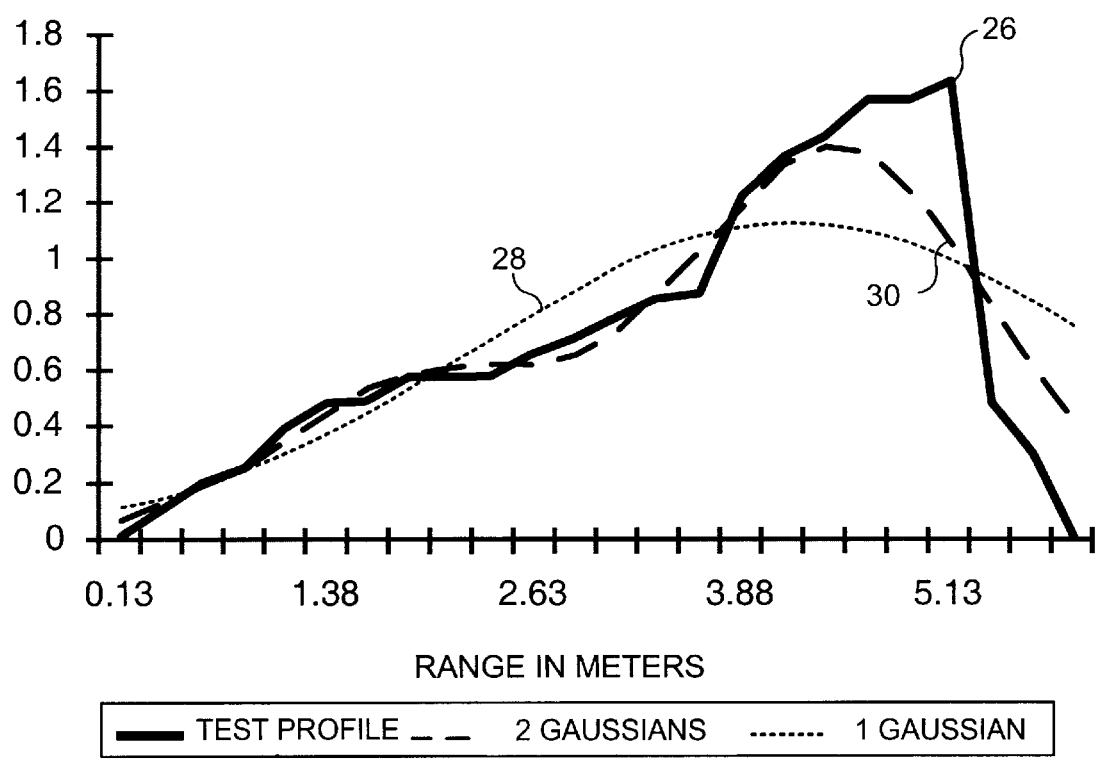
FIG. 4 is a graph showing differential reconstructions of the PIC data generated by the 1D beam geometry of FIG. 3, using both one and two Gaussian basis functions.

FIG. 4 illustrates a concentration map derived using data provided by the OP-FTIR instrument 22 and detectors (or reflectors) 12 configured as shown in FIG. 3A. Curve 26 represents the actual concentration levels as a function of distance from the OP-FTIR instrument within a planar sampling region. Curve 28 represents a single Gaussian directional derivative of the PIC data, while curve 30 represents two Gaussian directional derivatives of the PIC data. Note that each successive iteration more closely approximates the actual concentration levels of curve 26.

The preferred SBFM reconstruction approach requires a definition of an error function for minimization, in order to fit the observed PIC data to a set of predicted PIC values in terms of the basis function parameters. The predicted PIC values, which determine the resultant parameters of the basis functions for the radial beam geometry, are given by:

$$PIC_{predicted,i}(p_{jk}) = \sum_k \int_0^{L_i} G_k(r, \theta_i, p_{jk}) dr \qquad (1)$$

where i is the ray number index, j is the parameter number index, k is the basis function number index, $PIC_{predicted,i}$ is the $i^{th}$ predicted path integrated concentration updated in the iterative fitting procedure, $p_{jk}$ is the $j^{th}$ parameter of the $k^{th}$ basis function, $G_k(r, \theta_i, P_{jk})$ is the $k^{th}$ basis function in polar coordinates r and θ, and $L_i$ is the $i^{th}$ ray path length.

Preferably the Sum of Squared Errors (SSE) function is used to represent the global error between the observed PIC data and the calculated PIC values from the assumed smooth basis distribution. The SSE function defines a least squares criterion for the overall fit between the observed and predicted PIC values. The SSE function is given by:

$$SSE = \sum_i (PIC_{observed,i} - PIC_{predicted,i})^2 \qquad (2)$$

where $PIC_{observed,i}$ is the $i^{th}$ observed path integrated concentration along one beam path. The observed PIC values represent the input data measured by the optical remote sensing instrument. Minimizing the SSE function requires a computationally intensive iterative procedure to solve for the parameters of the basis functions. In some cases, the Simplex minimization method may suffice; otherwise, a more computationally costly minimization method, such as the Simulated Annealing minimization method should used to fit the basis functions, depending upon the quality of the results required.

To verify that the SBFM fitting method described above is capable of generating useful spatial concentration maps several different tests were conducted. First, synthetic data was used to construct spatial concentration maps from theoretical "real maps". Finally, controlled experiments were conducted in which concentration maps developed using a very sensitive point array detection system were compared with concentration maps of the same region developed using an OP-FTIR instrument and the SBFM fitting method described above.

The use of synthetic data to verify a computational technique is well known. By using synthetic data, rather than actual data, any error introduced in the detection process is eliminated. Thus, the potential of the computational technique being analyzed can be evaluated without the introduction of errors that are a function of the equipment used to execute the technique.

FIGS. 5A and 6A illustrate "real maps" 32 and 36, respectively, that were produced using theoretical data. The spatial shapes represented in these "real maps" correspond to distribution patterns that are commonly observed when mapping air pollutants. If actual spatial maps from previous investigations are available, the synthetic data process can be applied to those spatial maps also. Because the present invention is expected to be very useful in air pollution studies, concentration maps common to such studies provide a useful starting point in evaluating and verifying the preferred non-intersecting radial beam geometry and SBFM fitting method of the present invention.

Given a "real map," theoretically derived or actually measured, concentration data from the "real map" can be used to develop synthetic PIC data for a plurality of optical beam paths. The term synthetic refers to the fact that the PIC data has not been measured by an instrument (which would likely introduce some finite error), but rather has been "synthetically" derived from a known source (the real map), under the assumption that a geometry like that of FIG. 2 could have been used to produce the PIC data.

FIGS. 5B and 6B represent synthetic maps 34 and 38 of the "real maps" 32 and 36, respectively, of FIGS. 5A and 5B, obtained by simulating the use of the non-intersecting radial beam geometry of FIG. 2 to obtain synthetic PIC data for each optical beam path of FIG. 2 from the "real map," and applying the SBFM fitting method described above to the synthetic PIC data. It is apparent that while the "real maps" and the re-constructed synthetic maps are not identical, they are quite similar. Given that the prior art methods of obtaining such a concentration map required considerably more complex systems than the present invention, it is rather remarkable that an acceptably accurate concentration map can be provided by a considerably less complicated system of the present invention. In many cases, a reasonably accurate, easily obtainable concentration map is more desirable that a more accurate concentration map that is substantially more difficult to achieve. Air pollution monitoring is but one example of a field in which reasonably accurate and easy to produce concentration maps are quite desirable.

Once that the validity of the combination of the preferred radial beam geometry of FIG. 2 and the SBMF fitting technique had been established using synthetic data techniques discussed above, actual experimental data were collected to further validate the present invention. FIG. 7A illustrates a concentration map 40 of a plume of particles within a volume of air. The concentration map of FIG. 7A was generated using an array of point detectors within an exposure chamber (i.e., a controlled environment) with horizontal plug flow. While such an array of detectors is quite accurate, it is also quite costly and not well adapted to use outside an exposure chamber.

An OP-FTIR instrument (not shown in the graph) was positioned at a location (12.5, 0.5) relative to the X and Y axes in the exposure chamber (i.e., proximate the right corner of the X-Y plane of the graph). The non-intersecting radial beam geometry of FIG. 2 was used to generate PIC data, and the SBFM fitting technique was applied to the PIC data to produce a concentration map 42, illustrated in FIG. 7B. Unlike the concentration maps developed using synthetic data (see FIGS. 5B and 6B), the data used to construct concentration map 42 in FIG. 7B includes noise associated with the OP-FTIR instrument (and any associated detectors). While the concentration map of FIG. 7B is not identical to more accurate concentration map 40 in FIG. 7A, which was generated using an array of point sensors, concentration map 42 in FIG. 7B, which was produced using the present invention, is reasonably accurate.

Based on confirmation in the above and other experiments, it has been verified that concentration maps generated in accord with the present invention typically produce a peak location that varies less than 15% from that in concentration maps generated by an array of point sensors. The concordance correlation factor (CCF) has been shown to vary from a low of 0.51 to a high of 0.91, indicating that such re-constructed concentration maps produced with the present invention include 50–91% of the data present in a map generated by a complex array of point sensors. Given that the OP-FTIR instrument and the simple radial beam geometry of the present invention can be used in many field applications in which an array of point sensors could not be readily employed, the value of the present inventions in obtaining useful data in real world environments should be apparent. In fact, there are many potential applications in which the present invention can be used to provide a reasonably accurate concentration map, while prior art methods would be unable to provide any useful data.

FIG. 8 is a flow chart that illustrates the sequence of logical steps used in the present invention to produce a spatial concentration map using PIC data and a preferred curve fitting methodology. The logic begins at a start block 110 and proceeds to a block 112 in which the PIC data are obtained. In a preferred embodiment, the PIC data are obtained using an OP-FTIR instrument, although as described above, other types of instruments can alternatively be used. As previously noted, unless additional parameters are provided (such as the general location of the plume, or maximum concentration levels), at least six optical beams of differing path lengths should be used. It is further preferred that the non-intersecting radial beam paths illustrated in FIG. 2 be employed, although other beam geometries, including overlapping beams, can be used.

From block 112, the logic proceeds to a block 114, in which the PIC data are processed to mathematically fit the observed PIC data with predicted PIC values, either from discrete pixels or from a function, to obtain directional derivatives and to produce a set of discrete pixels or a smooth curve fitted to the resulting data. As discussed above, many different reconstruction or interpolation methods can be beneficially employed to fit the observed PIC data. A discrete pixel matrix, single functions, as well as spline functions can be used. From block 114, the logic proceeds to a decision block 116, and the logic determines if reiteration of the fitting procedure is required. In general, each successive iteration will provide a better fit. However, at some point, any increase in accuracy achieved in a each further iteration will yield only a marginal or no improvement. A logical point for terminating the iteration process is when the improvement in accuracy between successive iterations is less than the combined noise introduced by the illuminating source and the detectors (or reflectors).

If, at decision block 116, the logic determines that additional iterations are required, the logic loops back to block 114, and the pixel or function parameter values are altered so that the fitting procedure is repeated. If, at decision block 116, the logic determines that no additional fitting is required, the logic proceeds to an end block 118. At this point, a tomographical concentration map can be generated, as desired.

In addition to employing one of a variety of different fitting basis functions, those of ordinary skill in the art will recognize that interpolating the PIC data in the cumulative domain can be accomplished using a variety of approaches. There exist a variety of different minimization procedures that can be used to fit the PIC data, and other techniques can be employed to evaluate the directional derivatives to reconstruct the desired spatial properties. The present invention should not be considered to be limited to a particular interpolation technique, but instead, should be understood to encompass any related and appropriate manipulation of data derived from variable path length beam geometry where at least some beams terminate within the sampling region that produces a desired concentration map.

FIG. 9 is a flow chart that illustrates the sequence of logical steps used in the present invention in a preferred embodiment that employs the SBFM technique to fit the PIC data. The logic begins at a start block 120, and proceeds to a block 122 in which the PIC data are obtained. Again, preferably the PIC data are obtained using an OP-FTIR instrument, although other instruments can alternatively be used. The OP-FTIR is preferably mounted on a turntable or other gimbaled assembly (not shown) so that it can readily be sequentially aimed in different directions to produce the plurality of beam paths through the region of interest. If so, only a single OP-FTIR instrument and a plurality of detectors need be employed, as illustrated in FIG. 2.

From block 122, the logic proceeds to a block 124, and a first set of basis functions (for application to the PIC data) are selected. The logic then proceeds to a block 126, and the selected PIC data are processed to determine directional derivatives and to fit a curve to the PIC data using the SBFM technique discussed above. The logic proceeds to a block 128, in which the SSE function described above is calculated, and the parameters obtained in block 126 are updated.

From block 128, the logic proceeds to a decision block 130, and the logic determines if a critical value has been reached. If, at decision block 130, the logic determines that a critical value has not been reached, i.e., that the limit of potential improvement in accuracy has not been reached, additional iterations are required, and the logic loops back to block 126 and the SBFM fitting procedure is repeated. If, at decision block 130, the logic determines that a critical value has been reached and that no additional fitting is required, the logic proceeds to an end block 134. At this point, a tomographical concentration map can be generated, as desired.

It is contemplated that instruments collecting non-integrated path concentration data can also be used in conjunction with the present invention, instead of the OP-FTIR instrument. For example, it is expected that data generated from a lidar instrument and a simple radial beam geometry such as illustrated in FIG. 2 can be used to generate a spatial concentration map. The raw data would first be integrated to produce PIC data. The PIC data would then be processed using the interpolation methods described above (or other acceptable methods), consistent with the logical steps described in FIG. 8. Lidar is the optical analogue of radar. Instead of bouncing radio waves from a target, in the application as a source in the present invention, lidar uses short pulses of laser light to detect particles or gases in the atmosphere.

Figure 10:
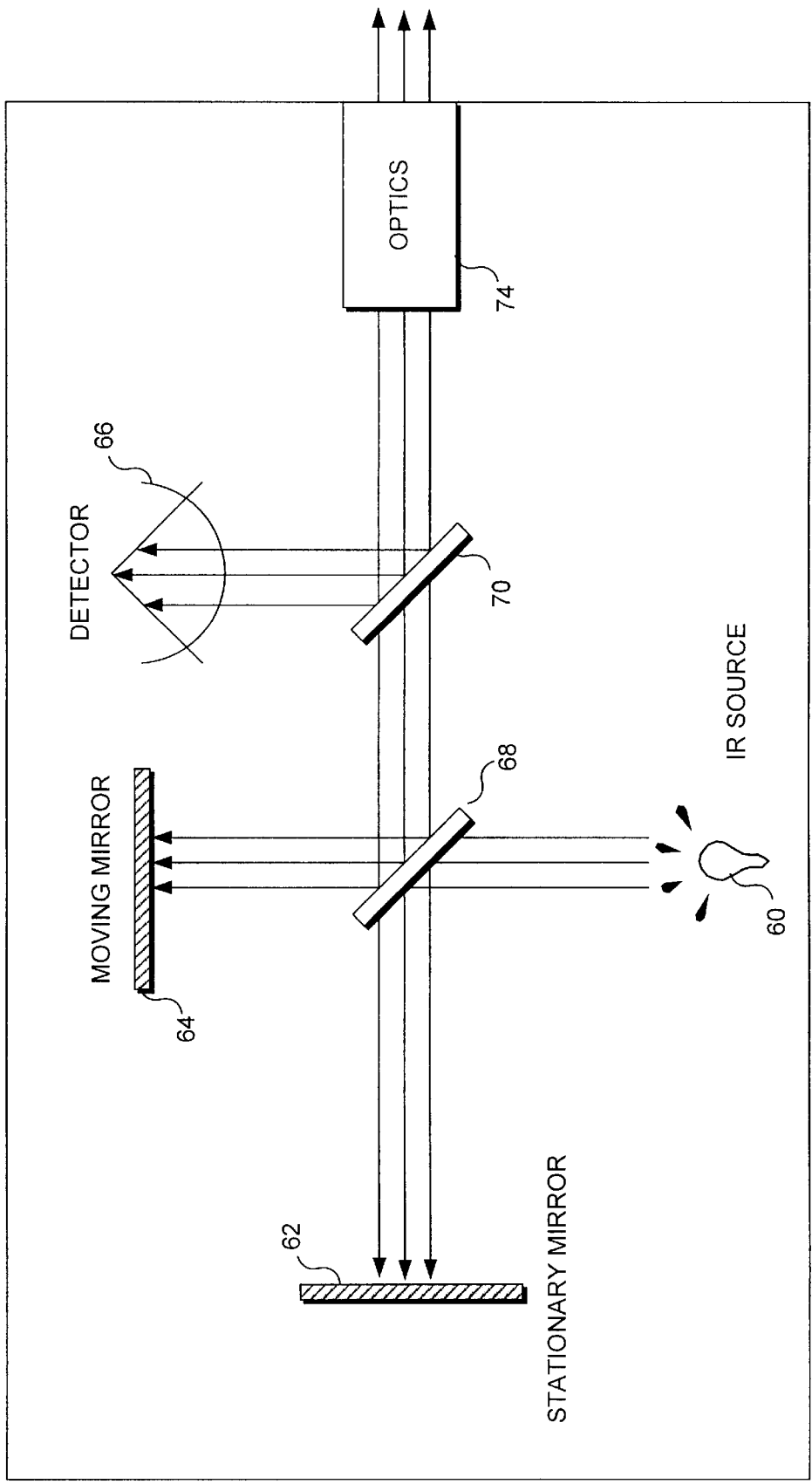

As noted above, a preferred embodiment employs an OP-FTIR instrument as the illuminating source. FIG. 10 is a schematic view of the functional elements in such the OP-FTIR instrument, which includes an infrared (IR) source 60, a stationary mirror 62, a moving mirror 64, a detector 66, an IR source beam splitter 68, a detector beam splitter 70, a housing 72, and optics 74. Note that optics 74 function both to focus IR light emitted from the instrument, as well as light returning to the instrument. The return light is focused and directed to detector 66. As noted above, IR wavelengths are particularly well suited for applications involving the study of gasses. IR source beam splitter 68, stationary mirror 62, and moving mirror 64 together form a Michelson interferometer, which is used to sample the optical energy in the frequency domain. Detector beam splitter 70 is used to direct the returned beam to detector 66. Because the detector is included in the same housing with the light source, mirrors or retroreflectors must be employed at the end of each beam path to return the emitted optical beams to the instrument.

FIGS. 11A and 11B illustrate OP-FTIR instruments in which the illuminating source and associated detectors are in the same housing.

FIG. 11A illustrates an instrument consistent with the OP-FTIR described in FIG. 10, in which a detector is disposed off the axis of the optical beam and a beam splitter is used to direct the optical beam to the detector. IR source 60, when appropriately energized, emits IR light that is directed into a Michelson interferometer 76, configured as described above, in connection with FIG. 10. The IR light exits the instrument through optics 74 and passes into a sampling region 78. The IR light that has passed through the sampling region is then redirected back toward the instrument by a corner retroflector 80. It is important that the IR light is returned to the instrument along a beam path that enables the light to pass through optics 74. If the returning light is not properly reflected, it will not pass through optics 74 and into detector 66, and useful data conveyed by the reflected light will be lost. However, corner retroreflector 80 inherently will direct the returning beam back along a nearly identical path that the light traveled from the source. Once the returning light passes through optics 74, it is directed to detector 66 by beam splitter 68.

FIG. 11B illustrates a variation of the OP-FTIR instrument shown in FIGS. 10 and 11A, in which a detector is disposed on the axis of the returning optical beam that is different than the axis of the IR light transmitted into the sampling region, and which does not use a beam splitter to direct the returning light to the detector. As with the instrument described in FIG. 11A, IR source 60 emits light that is directed into Michelson interferometer 76. The IR light exits the instrument through emitter optics 82 and passes into sampling region 78. The light is redirected back toward the instrument by a translating retroflector 84. Note that translating retroreflector 84 produces an offset returning beam path, such that the emitted beam and the returning beam are no longer traveling along nearly identical paths. The amount of offset required is a function of the physical dimensions of the OP-FTIR instrument, and more specifically, to the distance separating emitter optics 84 and receiving optics 86. Translating retroreflector 84 must be carefully selected so that the returning IR light is properly directed into receiving optics 86. Once the returning light passes through receiving optics 86, it is incident directly on detector 66.

FIGS. 12A and 12B illustrate OP-FTIR instruments for obtaining PIC data using distinct and separate housings 72' and 90 for the illuminating source and the detector, respectively. In FIG. 12A, the illuminating source includes Michelson interferometer 76, while in FIG. 12B the Michelson interferometer is associated with the detector in housing 90, not the IR source in housing 72'.

As shown in FIG. 12A, IR source 60 emits IR light that is directed into Michelson interferometer 76. The IR light exits the instrument through transmitting optics 82 and pass into sampling region 78. The IR light that has been transmitted through the sampling region is then directed onto a separate detector 88 by receiving optics 86. Note that separate detector 88 must be aligned along the emitted optical beam path, or mirrors must be used to redirect the emitted optical beam onto the separate detector.

FIG. 12B illustrates a variation of the OP-FTIR instrument shown in FIG. 12A, in which the Michelson interferometer is housed with the separate detector, rather than with the IR source. As noted above, IR source 60 emits IR light that exits the OP-FTIR instrument through transmitting optics 82. This IR light passes into sampling region 78, and is then into receiving optics 86 that are aligned with the emitted beam path. The IR light that is received is focused by receiving optics 86 into Michelson interferometer 76. Light from the interferometer, is directed onto separate detector 88.

Figure 13:
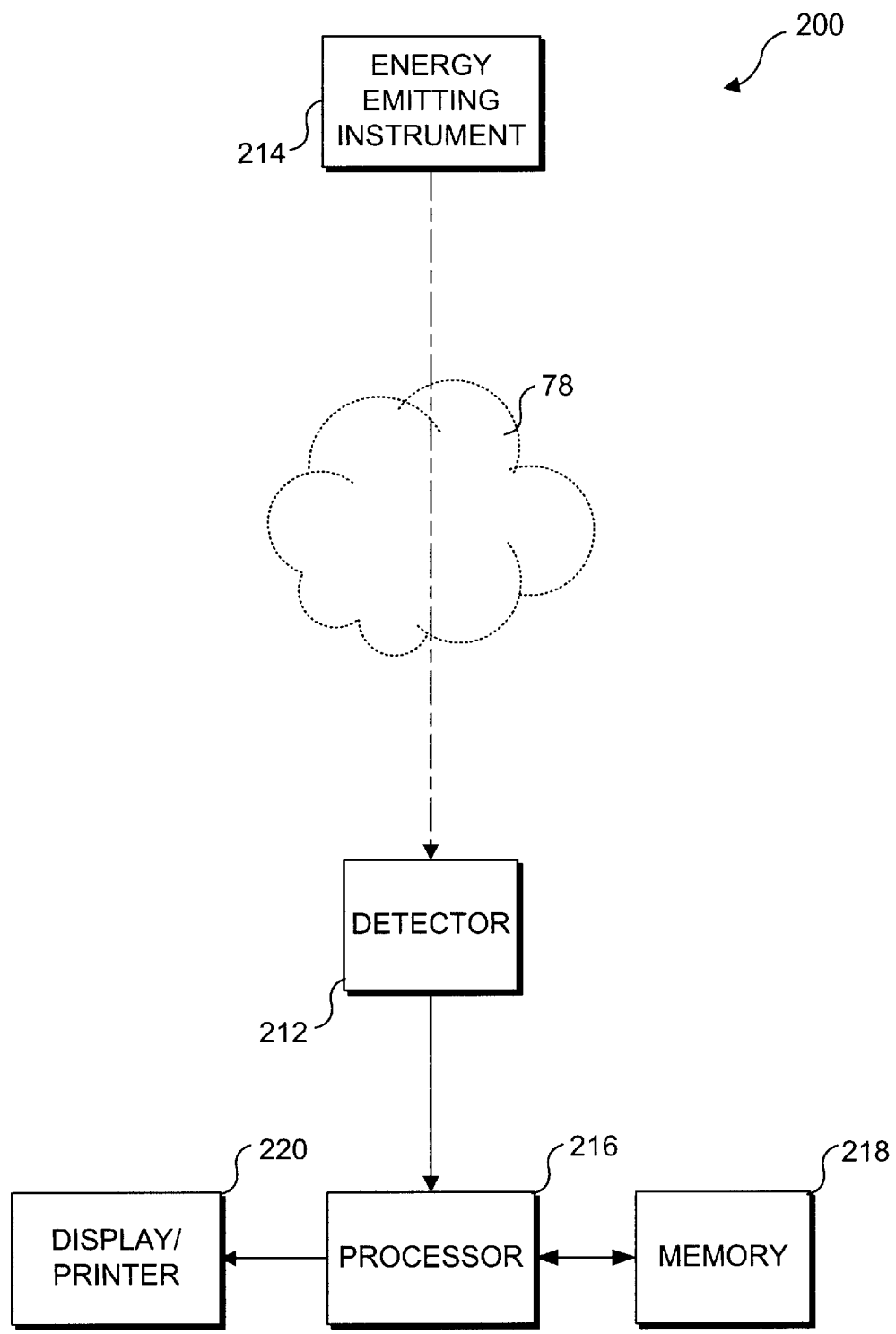
FIG. 13 illustrates the functional elements of a system for acquiring PIC data, generating a cumulative distribution function that fits the acquired PIC data, and producing a spatial concentration map in accord with the present invention.

FIG. 13 illustrates the functional elements of a system 200 for acquiring PIC data, generating a cumulative distribution function that fits the PIC data, and generating a map in accord with the present invention. An energy emitting instrument 214 emits a beam of energy directed along a path within sampling region 78. As noted above, in a preferred embodiment energy emitting instrument 214 is an optical instrument that emits light in the infrared ranges. However, other energy, such as acoustical energy, or other wavebands of light can also be beneficially employed. Detector 212 must be matched to the type of energy emitted by energy emitting instrument 214. While detector 212 is shown as a separate unit, as discussed above in relation to FIGS. 11A and 11B, detector 212 can be part of energy emitting instrument 214 if a suitable reflector (see FIGS. 11A and 11B) is used to direct the emitted energy into the detector. Note that while only one energy path is shown, it should be understood that the mapping process of the present invention requires the use of a plurality of energy beams. Preferably, these beams are sequentially generated, and the use of turntables, gimbals, and beam steering as discussed above enables a plurality of beam paths to be achieved.

Detector 212 is operatively coupled to a processor 216, which in turn is bidirectionally coupled to a memory 218. A plurality of machine instructions are stored in memory 218, to enable the system to acquire PIC data, generate a cumulative distribution function that fits the PIC data, and generate a spatial concentration map from the cumulative distribution function. A display/printer 220 is used to provide the user with an image of the spatial concentration map.

Although the present invention has been described in connection with the preferred form of practicing it and modifications thereto, those of ordinary skill in the art will understand that many other modifications can be made to the present invention within the scope of the claims that follow. Accordingly, it is not intended that the scope of the invention in any way be limited by the above description, but instead be determined entirely by reference to the claims that follow.

The invention in which an exclusive right is claimed is defined by the following:

1. A method of mapping a property associated with a sampling region using path integrated data, comprising the steps of:
    (a) defining a sampling region in which at least one property associated with said sampling region will be mapped;
    (b) acquiring path integrated data for a plurality of paths within said sampling region;
    (c) reiteratively generating a cumulative distribution function of said at least one property associated with said sampling region from said path integrated data; and
    (d) using said cumulative distribution function to produce a map of said property for the sampling region.

2. The method claim 1, wherein the step of acquiring path integrated data for a plurality of paths comprises the step of directing energy along the plurality of paths, such that at least one path terminates within said sampling region, and at least one different path extends to at least a boundary of said sampling region.

3. The method of claim 1, wherein the step of acquiring path integrated data for a plurality of paths comprises the step of directing energy along the plurality of paths, such that said plurality of paths do not intersect.

4. The method of claim 1, wherein the step of acquiring path integrated data for a plurality of paths comprises the step of directing energy along the plurality of paths, such that said plurality of paths radiate from a substantially common origin.

5. The method of claim 1, wherein the step of acquiring path integrated data for a plurality of paths comprises the step of directing energy along at least three different paths.

6. The method of claim 1, wherein the step of acquiring path integrated data for a plurality of paths comprises the step of directing energy along at least three different paths; and the step of reiteratively generating a cumulative distribution function comprises the step of combining a known parameter of said at least one property with the path integrated data to produce a cumulative distribution function.

7. The method of claim 6, wherein the property comprises a concentration of a constituent, and wherein the step of combining the known parameter of said at least one property with the path integrated data comprises the step of using one of a known concentration range of a constituent in said sampling region and a known disposition of said constituent in said sampling region.

8. The method of claim 1, wherein the step of acquiring path integrated data for a plurality of paths comprises the step maintaining a position of an energy source that emits energy along an axis, while varying a position of at least one energy detector along the axis, to provide a plurality of different length paths along the axis.

9. The method of claim 1, further comprising the step of emitting energy along the plurality of paths, and the step of acquiring path integrated data for the plurality of paths comprises the step of detecting the energy along each of a plurality of different length paths.

10. The method of claim 1, further comprising the step of emitting energy along the plurality of paths, and the step of acquiring path integrated data for the plurality of paths comprises the step of reflecting the energy back along each of a plurality of different length paths.

11. The method of claim 10, further comprising the step of sequentially emitting the energy in different directions, along each of the plurality of paths, wherein the step of acquiring path integrated data for the plurality of paths further comprises the step of detecting the energy that is reflected back along each of plurality of different length paths.

12. The method claim 11, further comprising the step of moving a source of the energy and an energy detector to sequentially emit the energy in different directions and to detect the energy that is reflected.

13. The method of claim 10, wherein the energy comprises one of light energy and acoustical energy.

14. The method of claim 1, wherein the sampling region is one of a gas, a liquid state, and a solid.

15. The method of claim 1, wherein the step of using said cumulative distribution function comprises the step of mapping a constituent concentration for the sampling region.

16. The method of claim 1, wherein the step of reiteratively generating said cumulative distribution function employs one of integrating over a discrete matrix of pixel values, a continuous function, a spline function matrix, and a smooth basis function minimization.

17. The method of claim 1, wherein the step of reiteratively generating said cumulative distribution function determines if an additional iteration is required as function of whether a predetermined limit has been achieved.

18. The method of claim 17, wherein the predetermined limit is a function of a level of noise associated with the step of acquiring the path integrated data.

19. A method of mapping contaminants within a sampling region using path integrated data, comprising the steps of:
   (a) providing an instrument capable of generating path integrated concentration (PIC) data within said sampling region;
   (b) using said instrument to acquire PIC data for a plurality of different paths within said sampling region;
   (c) reiteratively generating a cumulative distribution function that fits the acquired PIC data; and
   (d) using said cumulative distribution function to create a two-dimensional (2D) spatial map indicating levels of said contaminants within the sampling region.

20. The method of claim 19, wherein the step of providing an instrument comprises the step of providing an instrument that produces an illuminating signal that is one of an optical signal and an acoustic signal.

21. The method of claim 19, wherein the step of using said instrument to acquire PIC data comprises the steps of using said instrument to generate a first path having a first length, and then using said instrument to generate additional paths having different lengths.

22. The method of claim 21, wherein said instrument is used to generate at least three paths of different lengths.

23. The method of claim 19, wherein the step of using said instrument to acquire PIC data comprises the step of generating a plurality of non-intersecting paths.

24. The method of claim 19, wherein the step of using said instrument to acquire PIC data comprises the step of generating a plurality of paths that arrayed about a substantially common origin.

25. The method of claim 19, wherein the instrument comprises an illuminating unit and a detector, further comprising the step of providing a reflective unit that reflects a light signal emitted from said illuminating unit to said detector.

26. The method of claim 19, wherein the instrument comprises an illuminating unit and a detector, further comprising the step of providing a reflective unit for each of the plurality of paths that directs a signal emitted from said illuminating unit to said detector, the step of using said instrument to acquire PIC data comprising the step of varying an orientation of said instrument to determine directions of each of said plurality of different paths.

27. The method of claim 19, wherein the step of reiteratively generating the cumulative distribution function comprises the step of reiteratively generating a cumulative distribution function that is one of integrating over a discrete matrix of pixel values, a continuous function, a spline function matrix, and a smooth basis function minimization.

28. The method of claim 19, wherein the step of reiteratively generating the cumulative distribution function comprises the steps of determining if a level of improvement of a fit of the cumulative distribution function to the acquired PIC data between successive iterations exceeds a signal noise level associated with said instrument; and, if so, then continuing the step of reiteratively generating the cumulative distribution function.

29. The method of claim 19, wherein the step of reiteratively generating the cumulative distribution function comprises the step of including known parameters for said contaminant within said cumulative distribution function such that fewer paths are required to acquired the PIC data.

30. The method of claim 29, wherein the step of including known parameters of said contaminant within said cumulative distribution function comprises the step of including at least one of a location of said contaminant within said sampling region and a concentration range of said contaminant within said sampling region.

31. A system for acquiring path integrated concentration (PIC) data from within a sampling region and generating a spatial concentration map based on said PIC data, comprising:
   (a) an instrument that emits energy along a path;
   (b) at least one detector disposed so as to detect the energy emitted by said instrument, said detector producing a signal indicative of the PIC data along said path;
   (c) a memory in which a plurality of machine instructions are stored; and
   (d) a processor that is coupled to said at least one detector, and to said memory, said processor executing said machine instructions stored in the memory, causing the processor to implement a plurality of functions, including:
      (i) identifying a plurality of paths over which energy emitted by the instrument is directed and for which PIC data is obtained;
      (ii) accumulating PIC data for each path defined by the user;
      (iii) generating a cumulative distribution function that fits the accumulated PIC data; and
      (iv) using the cumulative distribution function to generate a spatial concentration map.

32. The system of claim 31, wherein said instrument comprises one of a Differential Optical Absorption Spectroscopy device, a Tunable Diode Laser device, a Differential Absorption Lidar device, a backscatter Lidar device and an Open Path Fourier Transformation Infrared Spectroscopy device.

33. The system of claim 31, wherein said sampling region comprises a volume of fluid.

34. The system of claim 31, wherein said energy comprises light.

35. The system of claim 31, wherein the instrument sequentially emits energy along a plurality of different paths.

36. The system of claim 31, further comprising a reflector disposed on an axis of the path along which said energy is emitted, wherein said at least one detector is disposed adjacent said instrument, such that said reflector reflects said energy to said at least one detector.

37. The system of claim 36, wherein said at least one detector comprises a single detector, and said single detector is incorporated within said instrument.

38. The system of claim 31, further comprising a one of a plurality of detectors and a detector array disposed within said sampling region.

39. The system of claim 31, wherein said instrument comprises an interferometer.

40. A method of mapping a property associated with a sampling region using path integrated data, to enable the property to be evaluated at specific locations over the measurement path without utilizing path integrated data obtained from intersecting sampling paths, comprising the steps of:

(a) defining a sampling region in which at least one property associated with said sampling region will be mapped;

(b) acquiring path integrated data for a plurality of sampling paths within said sampling region, such that the plurality of sampling paths are not required to intersect in order to obtain path integrated data that can be used to evaluate the at least one property at specific locations over each of the plurality of sampling paths;

(c) reiteratively generating a cumulative distribution function of the at least one property associated with said sampling region from said path integrated data, said cumulative distribution function enabling the at least one property to be evaluated at specific locations over each of the plurality of sampling paths without evaluating an average of the at least one property over a length of each of the plurality of sampling paths; and (d) using said cumulative distribution function to produce a map of the at least one property for the sampling region.

41. A method of mapping contaminants within a sampling region using path integrated data, comprising the steps of:

(a) providing an instrument capable of generating path integrated concentration (PIC) data within said sampling region;

(b) using said instrument to acquire PIC data for a plurality of different paths within said sampling region, such that none of the plurality of different paths are required to intersect in order to obtain the PIC data and so that said PIC data is usable to determine a contaminant concentration at specific locations over each of the plurality of sampling paths;

(c) reiteratively generating a cumulative distribution function that fits the acquired PIC data; and (d) using said cumulative distribution function to create a map of said contaminants within the sampling region.

42. A method of evaluating at least one property associated with a plurality of sampling paths using path integrated data, to enable the at least one property to be evaluated at specific locations over each sampling path, comprising the steps of:

(a) defining a sampling region in which at least one property associated with said sampling region will be mapped;

(b) acquiring the path integrated data for a plurality of sampling paths within said sampling region; and (c) reiteratively generating a cumulative distribution function of said at least one property associated with said sampling region from said path integrated data, said cumulative distribution function enabling the at least one property to be evaluated at specific locations over each of the plurality of sampling paths without evaluating an average of the at least one property over a length of each of the plurality of sampling paths.

43. A system for acquiring and evaluating at least one property associated with a plurality of sampling paths from within a sampling region using path integrated data, to enable the at least one property to be evaluated at specific locations over each sampling path, comprising:

(a) an instrument that emits energy along at least one path;

(b) at least one detector disposed so as to detect the energy emitted by said instrument, said detector producing a signal indicative of the path integrated data along said at least one path;

(c) a memory in which a plurality of machine instructions are stored; and (d) a processor that is coupled to said at least one detector, and to said memory, said processor executing said machine instructions stored in the memory, causing the processor to implement a plurality of functions, including:

(i) identifying a plurality of paths over which energy emitted by the instrument is directed and for which path integrated data are obtained;

(ii) accumulating the path integrated data for each path identified by the user;

(iii) generating a cumulative distribution function that fits the accumulated path integrated data; and (iv) using the cumulative distribution function to evaluate the at least one property at specific locations over each of the plurality of sampling paths.

\* \* \* \* \*

UNITED STATES PATENT AND TRADEMARK OFFICE
CERTIFICATE OF CORRECTION

PATENT NO. : 6,542,242 B1
DATED : April 1, 2003
INVENTOR(S) : Yost et al.

Page 1 of 1

It is certified that error appears in the above-identified patent and that said Letters Patent is hereby corrected as shown below:

<u>Column 1,</u>
Line 12, please add the following heading and paragraph:
-- GOVERNMENT RIGHTS
This invention was funded at least in part under a cooperative agreement
(No. DE-FC01-95EW55 084) with the Department of Energy (DOE), and the U.S. government may have certain rights in this invention. --

Signed and Sealed this

Second Day of August, 2005

JON W. DUDAS
*Director of the United States Patent and Trademark Office*